United States Patent [19]
Lee et al.

[11] Patent Number: 5,459,274
[45] Date of Patent: Oct. 17, 1995

[54] PREPARATION OF N-ALKYL-N-PYRIDINYL-1H-INDOL-1-AMINES

[75] Inventors: Thomas B. Lee, Whitehouse Station, N.J.; Keith E. Goehring, Nazareth, Pa.

[73] Assignee: Hoechst-Roussel Pharmaceuticals Inc., Somerville, N.J.

[21] Appl. No.: 242,395

[22] Filed: May 13, 1994

[51] Int. Cl.$^6$ ................................................. C07D 401/02
[52] U.S. Cl. ................................................................ 546/273
[58] Field of Search ............................................... 546/273

[56] References Cited

U.S. PATENT DOCUMENTS

| | | | |
|---|---|---|---|
| 4,618,686 | 10/1986 | Boyer | 549/360 |
| 4,752,610 | 6/1988 | Effland | 546/281 |
| 4,880,822 | 11/1989 | Effland | 514/339 |
| 4,970,218 | 11/1990 | Effland | 514/339 |
| 5,032,599 | 7/1991 | Effland | 546/256 |
| 5,039,811 | 8/1991 | Effland | 546/273 |

OTHER PUBLICATIONS

J. C. Powers, Journal of Organic Chemistry, 31, 2627 (1966) entitled "Chloroindoles" and published in the USA.

M. Somei and M. Natsume, Tetrahedron Letters, 461 (1974), entitled "1-Aminoindoles" and published in Great Britain.

M. R. Brennan, et al., Heterocycles, 24, 2879 (1986), entitled "The Preparation And Spectral Characterization of 2-Haloindoles, 3-Haloindoles, and 2,3-Dihaloindoles" and published in Japan.

G. M. Shutske, Medicinal Chemistry Approaches to Alzheimer's Disease and Other Dementias Symposium, Division of Educational Service, Mayo Clinic, Jacksonville, Jacksonville, Fla., Sep. 13, 1993.

M. Somei, et al., Chemical and Pharmaceutical Bulletin, 26, 2522 (1978), entitled "A Novel N-Amination Method and Its Application To the Preparation of N-Aminoheterocycles" and published in Japan.

D. L. Comins and M. O. Killpack, Tetrahedron Letters, 30, 4337 (1989), entitled "N-Methyl Lithiation of n-Methylindoles Directed By alpha-Amino Alkoxides" & published in the United Kingdom.

*Primary Examiner*—Jane Fan
*Attorney, Agent, or Firm*—Raymond R. Wittekind

[57] ABSTRACT

The synthesis of memory enhancing, analgetic, and antidepressant N-alkyl-N-pyridinyl-1H-indol-1-amines is described.

55 Claims, No Drawings

PREPARATION OF N-ALKYL-N-PYRIDINYL-1H-INDOL-1-AMINES

The synthesis of memory enhancing, analgetic, and antidepressant N-alkyl-N-pyridinyl-1H-indol-1-amines 1, involving arylation of a compound of formula 2

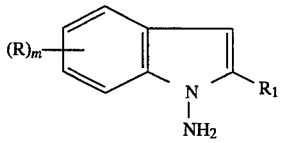

by a halopyridine of formula 3

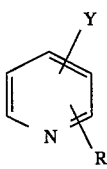

to provide an N-pyridinyl-1H-indol-1-amine of formula 4

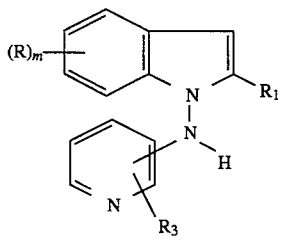

followed by alkylation of 4 by a compound of formula 5

R₂Z      5 to yield an ultimate N-alkyl-N-pyridinyl-1H-indol-1-amine of formula 1

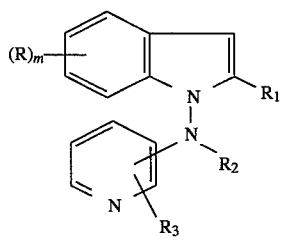

wherein R is hydrogen, loweralkyl or loweralkoxy; $R_1$ is hydrogen or loweralkyl; $R_2$ is loweralkyl; $R_3$ is hydrogen, loweralkyl or loweralkoxy; and m is 1 has been described. See, for example, U.S. Pat. No. 4,880,822 granted Nov. 14, 1989.

Applicants have now found that by starting with a 3-haloindole of formula 6

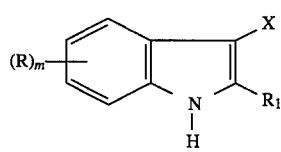

wherein R is as above and in addition is trifluoromethyl, $R_1$ is as above and m is as above and in addition is 2, prepared by halogenation of an indole of formula 7

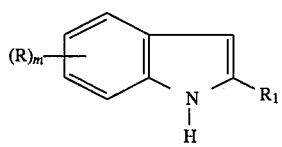

wherein R (including trifluoromethyl), $R_1$ and m (including 2) are as above with a halosuccinimide of formula 8

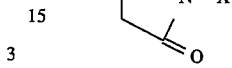

wherein X is bromo, chloro or iodo, aminating a 3-haloindole 6 to a 1-amino-3-haloindole 9

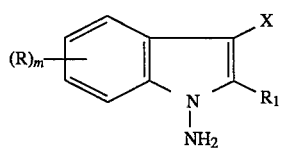

wherein R (including trifluoromethyl), $R_1$, X and m (including 2) are as above, arylating a 1-aminoindole 9, so obtained, with a halopyridine 3 wherein Y is a halogen to a 3-halo-N-pyridinylaminoindole 10

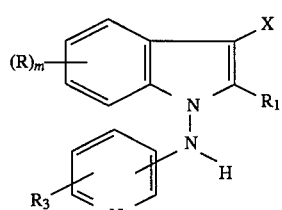

wherein R (including trifluoromethyl), $R_1$, $R_3$, X and m (including 2) are as above, alkylating an N-pyridinylaminoindole 10, so obtained, to an N-alkyl-3-halo-N-pyridinylaminoindole 11

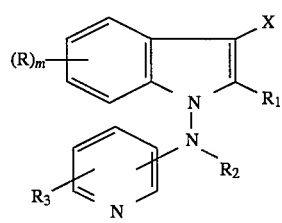

wherein R (including trifluoromethyl), $R_1$, $R_2$, $R_3$, X and m (including 2) are as above, and finally dehalogenating an N-alkyl-3-halo-N-pyridinylaminoindole 11, so obtained, an ultimate N-alkyl-N-pyridinyl-1H-indol-1-amine 1 wherein R (including trifluoromethyl), $R_1$, $R_2$, $R_3$ and m (including 2) are as above is obtained in high overall yield, even though a halo group is introduced in the first step of the sequence and removed in the last step to form the final product. In addition, costly, time consuming, yield reducing chromatographic separations and purifications are avoided in the present process to prepare the desired pharmacological product.

Thus, the present invention relates to a process for the preparation of memory enhancing, analgetic and antidepressant N-alkyl-N-pyridinyl-1H-indole-1-amines. More particularly, the present invention relates to a process for the preparation of memory enhancing, analgetic and antidepressant N-alkyl-N-pyridinyl-1H-indol-1-amines of formula 1 involving the steps of halogenating a commercially available or readily preparable indole 7 to a 3-haloindole 6, aminating a 3-haloindole 6 to a 1-amino-3-haloindole 9, arylating a 1-amino-3-haloindole 9 to a 3-halo-N-pyridinylaminoindole 10, alkylating a 3-halo-N-pyridinylaminoindole 10 to an N-alkyl-3-halo-N-pyridinylaminoindole 11 and dehalogenating an N-alkyl-3-halo-N-pyridinylaminoindole 11 to an N-alkyl-N-pyridinylaminoindole 1, wherein R, $R_1$, $R_2$, X and M are as described immediately above.

The present process is most particularly useful for the preparation of N-alkyl-N-pyridinyl-1H-indole amines 1 wherein R is hydrogen; $R_1$ is hydrogen, $R_2$ is loweralkyl, $R_3$ is hydrogen and m is 1, and still most particularly wherein $R_2$ is n-propyl.

The halogenation of an indole 7 to a 3-haloindole 6 is accomplished by methods known in the art, for example, by the use of an N-halosuccinimide 8 such as N-chlorosuccinamide in an aprotic dipolar solvent, such as dimethylformamide at a reaction temperature of about 10° to 18° C.

The amination is achieved by contacting a 3-haloindole 7 with hydroxylamine-O-sulfonic acid in a dipolar aprotic solvent in the presence of a base or bases. Among dipolar aprotic solvents, there may be mentioned dimethylacetamide, dimethylformamide, N-methyl-2-pyrrolidinone, dimethylsulfoxide and hexamethylphosphoramide, dimethylformamide being preferred. Among bases, there may be mentioned, alkali metal hydroxides and alkali metal carbonates, such as lithium, sodium and potassium hydroxides and lithium, sodium and potassium carbonates, respectively. Potassium hydroxide is the preferred base. A mixture of potassium hydroxide and potassium carbonate is the preferred mixture of bases. The amination reaction temperature is not narrowly critical; the reaction proceeds at a satisfactory rate at a reduced temperature of about −10° to about 20° C., an amination temperature of about 0° to about 10° being preferred.

The arylation is effected by contacting a 1-amino-3-haloindole 9 with a halopyridine 3, as the free base or hydrohalide salt, preferably a hydrochloride salt, in a dipolar aprotic solvent such as, for example, dimethylformamide, dimethylacetamide, dimethylsulfoxide, hexamethyl phosphoramide, and N-methyl-2-pyrrolidinone, N-methyl-2-pyrrolidinone being preferred. The arylation proceeds at a reasonable rate at a reaction temperature within the range of about 60° to 120° C., an arylation temperature of about 80° C. being preferred.

A 3-halo-N-pyridinylindolamine 10, is isolated as a benzoate salt, preferably the salicylate salt, prepared by treating a 3-halo-N-pyridinylindolamine 10, with a benzoic acid, preferably salicylic acid, in an alkyl alkanoate, preferably ethyl acetate, at ambient temperature.

The alkylation is achieved by reacting a 3-halo-N-pyridinylindolamine 10, with an alkyl halide 5, preferably an alkyl bromide, in a dipolar aprotic solvent (e.g., dimethylacetamide, dimethylformamide, dimethylsulfoxide, hexamethylphosphoramide, or N-methyl-2-pyrrolidinone) in the presence of a base (e.g., an alkali metal alkoxide, such as a lithium, sodium or potassium alkoxide). Dimethylformamide is the preferred solvent. Potassium tert-butoxide is the preferred base.

The alkylation is preferably performed at reduced temperatures within the range of about −10° to about 0° C. Alkylation temperatures within the range of about −20° to about 20° may be employed to effect the conversion.

When a benzoate salt of a 3-halo-N-pyridinylindolamine 10 is used in the alkylation step, the salt, preferably the salicylate salt, is converted to the free base by treatment with an alkali metal hydroxide, such as sodium hydroxide, in an aromatic solvent, such as toluene,, by ordinary methods.

An N-alkyl-3-halopyridinylindolamine 11 is isolated as a hydrohalide salt, preferably the hydrochloride salt, prepared by treating an N-alkyl-3-halopyridinylindolamine 11 with a hydrogen halide, preferably hydrogen chloride, in an ethereal solvent, preferably diethyl ether.

The final step of the sequence, the dehalogenation of an N-alkyl-3-halo-N-pyridinylindolamine 11 to a pharmacologically active N-alkyl-N-pyridinylindolamine 1 is accomplished by contacting an N-alkyl-3-halo-N-pyridinylindolamine 11 with formic acid in the presence of a metal catalyst in an alkanol. Among alkanols, included are methanol, ethanol, 1- and 2-propanols, 1,1-dimethylethanol and the like. 2-Propanol is preferred. Included among metal catalysts are palladium-on-carbon, Raney nickel, tetrakistriphenylphosphine palladium (0) and palladium acetate. Palladium-on-carbon is preferred.

The dehalogenation is carded out at elevated temperature, preferably the reflux temperature of the reaction medium, although it proceeds at a reasonable rate at lower temperatures.

The dehalogenation may also be carded out on a hydrohalide salt, preferably the hydrochloride, of an N-alkyl-3-halo-N-pyridinylindolamine 11. When a hydrohalide salt is used, a tertiary amine (e.g., triethylamine, pyridine, picoline, lutidine, s-collidine, and the like) is employed to convert the salt to the free base.

An N-alkyl-N-pyridinylindolamine 11 is characterized as a hydrohalide salt, preferably the hydrochloride salt, prepared by treating an indolamine 11 with a hydrohalic acid in an alkanol/ether, preferably methanol/methyl tert-butyl ether, under ordinary conditions.

As used throughout the specification and appended claims, the term "alkyl" refers to a straight or branched chain hydrocarbon radical containing no unsaturation and having 1 to 8 carbon atoms such as methyl, ethyl, 1-propyl, 2-propyl, 1-butyl, 1-pentyl, 2-pentyl, 3-hexyl, 4-heptyl, 2-octyl, and the like; the term "alkanol" refers to a compound formed by a combination of an alkyl group and a hydroxy radical. Examples of alkanols are methanol, ethanol, 1- and 2-propanol, 1,1-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like; the term "halogen" refers to a member of the family consisting of chlorine, bromine, iodine and fluorine. The term "lower" as applied to any of the aforementioned groups refers to a group having a carbon skeleton containing up to and including 6 carbon atoms.

The following examples are for illustrative purposes only and are not to be consumed as limiting the invention. All temperatures are given in degree centigrade (°C.).

EXAMPLE 1

Preparation of 3-chloroindole

To a 3 L round bottom flask equipped with a mechanical stirrer, thermometer and a Gooch tube was added sieve-dried dimethylformamide (1.2 L) and indole (200 g). The solution was stirred under an atmosphere of nitrogen and cooled to about 10° C. N-Chlorosuccinamide (216.6 g) was added via the Gooch tube at a rate such as to maintain a reaction temperature of 10°–18° C. After the addition was complete, a second charge of N-chlorosuccinamide (34.2 g) was added. When the reaction was found to be >97% complete by high performance liquid chromatography, the reaction mixture was poured into a well-stirred, cold solution of aqueous sodium bisulfite (5.2 L of 0.1% sodium bisulfite in water and 640 g of ice). After about 15 min, the precipitate was collected and washed with water (2×1 L). The filtrate was partitioned between dichloromethane (1.3 L) and 0.1% aqueous sodium bisulfite solution (1 L). The phases were separated and the aqueous solution was extracted with dichloromethane (300 ml). The organic fractions were combined, washed with water (800 mL), dried over anhydrous magnesium sulfate, filtered and the filtrate was concentrated (at about 25° C. and about 50 mm Hg). The residue was dried in a vacuum oven at 25° C. and about 125 mm Hg for 2 to 4 hrs to yield 240.3 g (92.9%) of product, 3-chloroindole (91.6% pure).

EXAMPLE 2

Preparation of 3-chloro-1H-indol-1-amine

To a 12 L round bottom flask equipped with a mechanical stirrer, thermometer and a Gooch tube was added sieve-dried dimethylformamide (2.8 L), 3-chloroindole (240 g, 91.6% pure), milled potassium carbonate (200.4 g), milled potassium hydroxide (574.3 g, 85% pure) and dimethylformamide (900 mL) at −2° to 5° C. The reaction mixture was cooled to about 0° C. and hydroxylamine-O-sulfonic acid (338.2 g, 97% pure) was added portionwise via the Gooch tube over a period of about 4 hrs, maintaining the reaction temperature at about 0° C. When the reaction was >95% complete (by high performance liquid chromatography), the reaction mixture was poured into a well-stirred, cold mixture of water (18 L and 3.6 kg ice) and toluene (2.4 L). After about 5 mins, the phases were separated and the aqueous phase was extracted with toluene (1×2.4 L and 1×1 L). The organic fractions were combined and filtered through Celite. The filtrate was concentrated under reduced pressure (about 50 mm Hg) at about 60° C. to yield 245 g (86%) of product.

EXAMPLE 3

Preparation of 3-chloro-N-4-pyridinyl-1H-indol-1-amine salicylate

A mixture of 3-chloro-1H-indol-1-amine (100 g), 1-methyl-2-pyrrolidinone (490 mL) and 4-chloropyridine hydrochloride (75.9 g, 96.2% pure) was heated at about 80° C., with stirring, under nitrogen, for 2 hrs. When the reaction was 88–89% complete, the reaction mixture was cooled to room temperature and poured into a well-stirred mixture of 5% sodium hydroxide solution (1.2 L) and toluene (800 mL). The mixture was stirred for 15 mins, filtered through Celite, and the phases of the filtrate were separated. The aqueous phase was extracted with toluene (1×400 mL and 1×200 mL). The organic fractions were combined and washed with water (800 mL). The emulsion was filtered through Celite and the phases were separated. The organic phase was dried over anhydrous potassium carbonate, filtered and the filtrate was concentrated at 50°–60° C. under reduced pressure (about 50 mm Hg) to provide 131.5 g of product as the free base.

The product, 3-chloro-N-4-pyridinyl-1H-indol-1-amine, was dissolved in ethyl acetate (745 mL) and filtered. The filtrate was added to a 2 L round bottom flask equipped with a mechanical stirrer. Salicylic acid (80.7 g) was added, with stirring, under a nitrogen atmosphere at room temperature. After stirring the mixture at room temperature for 2 hrs, the precipitate was collected and the filter cake was washed with cold (0°–5° C.) ethyl acetate (30 mL) and dried at 68°–70° C. (125 mm Hg) for 16 hrs to give 90.0 g (48.4%) of product, 3-chloro-N-4-pyridinyl-1H-indol-1-amine salicylate (99% pure), mp of 185°–186° C.

EXAMPLE 4

Preparation of 3-chloro-N-propyl-N-4-pyridinyl-1H-indol-1-amine hydrochloride

A solution of 3-chloro-N-4-pyridinyl-1H-indol-1-amine salicylate (10 g), toluene (100 mL) and 5% aqueous sodium hydroxide solution (100 mL) was filtered through Celite and the phases were separated. The aqueous phase was extracted with toluene (50 mL), and the combined organic phase was washed with water (75 mL), dried over anhydrous potassium carbonate, filtered and the filtrate was concentrated (50° C. bath, 50 mm Hg) to give the free base, 3-chloro-N-4-pyridinyl-1H-indol-1-amine.

To a 125 mL round bottom flask equipped with a mechanical stirrer, thermometer and a Gooch tube was added sieve-dried dimethylformamide (36 mL) and 3-chloro-N-4-pyridinyl-1H-indol-1-amine (4.5 g). The solution was cooled to about −10° C., with stirring, under a nitrogen atmosphere. Potassium-τ-butoxide (2.29 g) was added via the Gooch tube at a rate such as to maintain a reaction temperature of about −10° C. After the addition was complete, the mixture was allowed to warm to about 0° C. and age for about 1 hr. The Gooch tube was replaced with a dropping funnel and a solution of 1-bromopropane (2.96 g) in dry dimethylformamide (8.8 mL) was added at a rate such as to maintain a reaction temperature of about 0° C. When the reaction was 98% complete, the reaction mixture was poured into a stirred mixture of cold water (72 mL) and ethyl acetate (30 mL). The phases were separated and the aqueous phase was extracted with ethyl acetate (2×30 mL). The combined organic phase was washed with water (50 mL), dried over anhydrous magnesium sulfate, filtered and the filtrate was concentrated (at about 40° C. bath temperature and about 50 mm Hg) to yield 5.1 g (96.2%) of product as the free base (88.6% pure).

To a 4 g sample of product, 3-chloro-N-propyl-N-4-pyridinyl-1H-indol-1-amine, dissolved in anhydrous ether (60 mL) in a 125 mL-round bottom flask equipped with a mechanical stirrer, thermometer and dropping funnel, was added slowly an ethereal solution saturated with hydrogen chloride (6 mL) at room temperature, under a nitrogen atmosphere, with stirring. After about 0.5 hrs at room temperature, the precipitate was collected, washed with anhydrous ether (15 mL) and dried to yield 3.95 g (87.6%) of product.

EXAMPLE 5

Preparation of N-propyl-N-4-pyridinyl-1H-indol-1-amine hydrochloride

To a mixture of 3-chloro-N-propyl-N-4-pyridinyl-1H-indol-1-amine hydrochloride (500 mg), triethylamine (408 mg) and 5% palladium-on-carbon (34.7 mg) in 2-propanol (2.5 mL) was added, under a nitrogen purge, 98% formic acid (0.068 mL) via a syringe, with stirring. After the addition was complete, the reaction mixture was heated to reflux. Additional amounts of 5% palladium-on-carbon (104 mg), triethylamine (0.22 mL) and formic acid (0.028 mL) were added over 7.5 hrs in 3 portions. The mixture was cooled to room temperature, filtered through Celite and the filter cake was washed with 2-propanol (about 30 mL). The filtrate was concentrated under reduced pressure (50 mm Hg) and the residue partitioned between toluene (8 mL) and 5% aqueous sodium hydroxide solution (8 mL). The aqueous phase was separated and extracted with toluene (5 mL). The organic fractions were combined, washed with water (10 mL), dried over anhydrous magnesium sulfate and filtered. The filtrate was concentrated under reduced pressure (50 mm Hg) at 60° C. to yield 310 mg (79.5%) of the product, as the free base, (99% pure).

To a 25 mL round bottom flask equipped with a mechanical stirrer, thermometer and condenser was added N-propyl-N-4-pyridinyl-1H-indol-1-amine (2.1 g), methanol (2 mL), and 36–37% hydrochloric acid (0.66 mL), with stirring, at room temperature. The reaction mixture was seeded with product prepared previously and, after 5 mins, methyl-t-butyl ether (8.0 mL) was added, with stirring. The reaction mixture was allowed to cool to room temperature, then cooled to about 0° C. The precipitate was collected and the filter cake was washed with cold 1:4 methanol/methyl-t-butyl ether (2 mL), followed by methyl-t-butyl ether (6 mL) and dried at 85° C. (25 inches of mercury) to yield 2.07 g (88.6%) of product.

The determination of the purity of the reactants and the products of the examples was determined in a Perkin-Elmer 410/Kratos Spectroflow 783 high performance liquid chromatograph using a Phenomenex Bondclone 10C18 (3.9×300 mm) column with a mobile phase of 50:50 acetonitrile/0.1N aqueous ammonium formate solution at a flow rate of 1.5 mL/min. with detection at 255 nm. Samples were prepared in acetonitrile, filtered and applied to the column.

We claim:

1. A process for the preparation of a compound of the formula

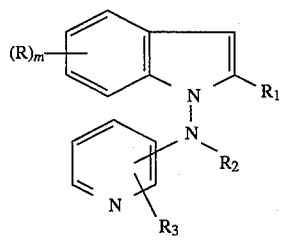

wherein R is hydrogen, loweralkyl, loweralkoxy or trifluoromethyl; $R_1$ is hydrogen or loweralkyl; $R_2$ is loweralkyl; $R_3$ is hydrogen, loweralkyl, loweralkoxy or trifluoromethyl; and m is 1 or 2, which comprises the steps of:

(a) reacting a compound of the formula

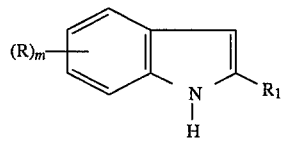

wherein R, $R_1$ and m are as above with a compound of the formula

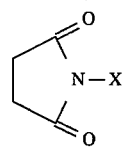

wherein X is bromo, chloro or iodo to provide a compound of the formula

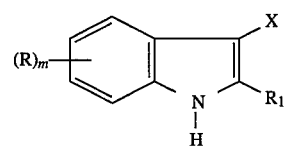

wherein R, $R_1$, X and m are as above;

(b) reacting the compound obtained in step (a) with a compound of the formula $H_2NOSO_3H$ to provide a compound of the formula

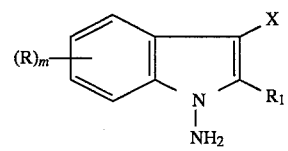

wherein R, $R_1$, X and m are as above;

(c) reacting a compound obtained in step (b) with a compound of the formula

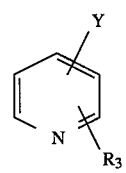

wherein $R_3$ is as above and Y is chloro, bromo or iodo to provide a compound of the formula

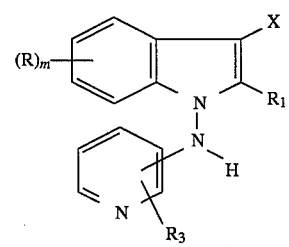

wherein R, $R_1$, $R_3$, X and m are as above;

(d) reacting a compound obtained in step (c) with a compound of the formula $R_2Z$ wherein $R_2$ is as above and Z is bromo or chloro to provide a compound of the formula

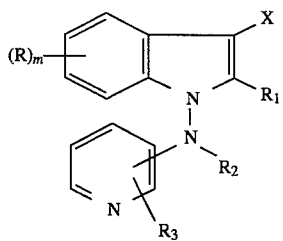

wherein R, $R_1$, $R_2$, $R_3$, X and m are as above;
(e) reacting a compound obtained in step (d) with formic acid in the presence of a metal catalyst; and
(f) isolating the product.

2. A process according to claim 1 wherein R is hydrogen; $R_1$ is hydrogen; $R_2$ is loweralkyl; $R_3$ is hydrogen and m is 1.

3. The process according to claim 2 wherein $R_2$ is n-propyl.

4. A process according to claim 1 wherein X and Y are chloro and Z is bromo.

5. A process according to claim 1 wherein a solvent is employed in step (a).

6. A process according to claim 5 wherein the solvent is a dipolar aprotic solvent.

7. The process according to claim 6 wherein the dipolar aprotic solvent is dimethylformamide.

8. A process according to claim 1 wherein a base or a mixture of bases is employed in step (b).

9. A process according to claim 8 wherein the base is an alkali metal hydroxide.

10. The process according to claim 9 wherein the alkali metal hydroxide is potassium hydroxide.

11. A process according to claim 8 wherein the mixture of bases is an alkali metal hydroxide and an alkali metal carbonate.

12. The process according to claim 11 wherein the alkali metal hydroxide is potassium hydroxide and the alkali metal carbonate is potassium carbonate.

13. A process according to claim 1 wherein a solvent is employed in step (b).

14. A process according to claim 13 wherein the solvent is a dipolar aprotic solvent.

15. The process according to claim 14 wherein the dipolar aprotic solvent is dimethylformamide.

16. A process according to claim 1 wherein a solvent is employed in step (c).

17. A process according to claim 16 wherein the solvent is a dipolar aprotic solvent.

18. The process according to claim 17 wherein the dipolar aprotic solvent is 1-methyl-2-pyrrolidinone.

19. A process according to claim 1 wherein the product of step (c) is treated with a benzoic acid in a loweralkyl alkanoate to form a benzoate salt thereof.

20. The process according to claim 19 wherein the benzoic acid is salicylic acid and the loweralkyl alkanoate is ethyl acetate.

21. A process according to claim 1 wherein a solvent is employed in step (d).

22. A process according to claim 21 wherein the solvent is a dipolar aprotic solvent.

23. The process according to claim 22 wherein the dipolar aprotic solvent is dimethylformamide.

24. A process according to claim 1 wherein a benzoate salt of the compound obtained in step (c) is employed in step (d).

25. A process according to claim 24 wherein the benzoate salt is a salicylate salt.

26. A process according to claim 24 wherein the benzoate salt is converted to the compound obtained in step (c).

27. A process according to claim 26 wherein an aromatic solvent and an aqueous solution of an alkali metal hydroxide are employed.

28. The process according to claim 27 wherein the aromatic solvent is toluene and the alkali metal hydroxide is sodium hydroxide.

29. A process according to claim 1 wherein a base is employed in step (d).

30. A process according to claim 29 wherein the base is an alkali metal alkoxide.

31. The process according to claim 30 wherein the alkali metal alkoxide is potassium tert-butoxide.

32. A process according to claim 1 wherein the compound obtained in step (d) is treated with a hydrohalide in an ethereal solvent to form a hydrohalide salt thereof.

33. The process according to claim 32 wherein the hydrohalide is hydrogen chloride and the ethereal solvent is diethyl ether.

34. A process according to claim 1 wherein the metal catalyst employed in step (e) is selected from the group consisting of palladium-on-carbon, Raney nickel, tetrakistriphenylphosphine palladium (0), and palladium acetate.

35. The process according to claim 34 wherein the palladium-on-carbon is 5% palladium-on-carbon.

36. A process according to claim 1 wherein a solvent is employed in step (e).

37. A process according to claim 36 wherein the solvent is an alkanol.

38. The process according to claim 37 wherein the alkanol is 2-propanol.

39. A process according to claim 1 wherein a hydrohalide salt of a compound obtained in step (d) is employed in step (e).

40. The process according to claim 39 wherein the hydrohalide salt is the hydrochloride salt.

41. A process according to claim 1 wherein a base is employed in step (e) when a hydrohalide salt of the compound obtained in step (d) is used.

42. A process according to claim 41 wherein the base is a tertiary amine.

43. The process according to claim 42 wherein the tertiary amine is triethylamine.

44. The process according to claim 41 wherein the hydrohalide salt is the hydrochloride salt.

45. A process according to claim 1 wherein the compound obtained in step (e) is treated with a hydrohalic acid in an alkanol to form a hydrohalide salt thereof.

46. The process according to claim 45 wherein the hydrohalic acid is hydrochloric acid.

47. The process according to claim 45 wherein the alkanol is methanol.

48. A process according to claim 1 wherein the reaction of step (a) is performed at a temperature of from about 10° to about 18° C.

49. A process according to claim 1 wherein the reaction of step (b) is performed from about −10° to 20° C.

50. The process according to claim 49 wherein the reaction of step (b) is performed at about 0° C. to 10° C.

51. A process according to claim 1 wherein the reaction of step (c) is performed within the range of about 60° to about 120° C.

52. The process according to claim 51 wherein the reaction is performed at about 80° C.

53. A process according to claim 1 wherein the reaction of step (d) is performed within the range of about −20° to about 20° C.

54. The process according to claim 53 wherein the reaction temperature is about −10° C. to about 0° C.

55. A process according to claim 1 wherein the reaction of step (e) is performed at a temperature of about the reflux temperature of the reaction medium.

* * * * *